United States Patent
Georgakis et al.

(10) Patent No.: US 6,554,612 B2
(45) Date of Patent: Apr. 29, 2003

(54) ORTHODONTIC BRACKET WITH RECESSED ATTACHMENT AND METHOD FOR MAKING THE SAME

(75) Inventors: Evangelos G. Georgakis, Alta Loma, CA (US); Oliver L. Puttler, La Crescenta, CA (US); Ming-Lai Lai, Arcadia, CA (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/888,745

(22) Filed: Jun. 25, 2001

(65) Prior Publication Data

US 2002/0197581 A1 Dec. 26, 2002

(51) Int. Cl.[7] .................................. A61C 3/00
(52) U.S. Cl. ........................................ 433/11
(58) Field of Search ................. 433/8, 9, 10, 11, 433/13, 14, 22

(56) References Cited

U.S. PATENT DOCUMENTS

| | | | |
|---|---|---|---|
| 1,991,047 A | | 2/1935 | Boyd et al. |
| 2,713,720 A | | 7/1955 | Johnson |
| 3,327,393 A | | 6/1967 | Brader |
| 3,959,880 A | * | 6/1976 | Andrews ............... 433/8 |
| 4,077,126 A | * | 3/1978 | Pletcher ............... 433/10 |
| 4,103,423 A | | 8/1978 | Kessel |
| 4,149,314 A | | 4/1979 | Nonnenmann |
| 4,197,642 A | | 4/1980 | Wallshein |
| 4,260,375 A | | 4/1981 | Wallshein |
| 4,419,078 A | * | 12/1983 | Pletcher ............... 433/10 |
| 4,496,318 A | | 1/1985 | Connelly, Jr. |
| 4,559,012 A | | 12/1985 | Pletcher |
| 4,698,017 A | | 10/1987 | Hanson |
| 4,917,602 A | * | 4/1990 | Broussard ............... 433/8 |
| 4,954,080 A | | 9/1990 | Kelly et al. |
| 5,322,435 A | | 6/1994 | Pletcher |
| 5,358,402 A | | 10/1994 | Reed et al. |
| 5,380,196 A | | 1/1995 | Kelly et al. |
| 5,395,237 A | | 3/1995 | Pospisil et al. |
| 5,439,379 A | | 8/1995 | Hansen |
| 5,466,151 A | | 11/1995 | Damon |
| 5,516,284 A | | 5/1996 | Wildman |
| 5,522,725 A | | 6/1996 | Jordan et al. |
| 5,597,302 A | | 1/1997 | Pospisil et al. |
| 5,685,711 A | | 11/1997 | Hanson |
| 5,711,666 A | | 1/1998 | Hanson |
| 5,913,680 A | | 6/1999 | Voudouris |
| 6,042,373 A | * | 3/2000 | Hermann ............... 433/13 |
| 6,168,428 B1 | | 1/2001 | Voudouris |
| 6,193,508 B1 | | 2/2001 | Georgakis |

FOREIGN PATENT DOCUMENTS

WO    WO 01/22901    4/2001

OTHER PUBLICATIONS

Pending U.S. patent application Ser. No. 09/848,030.

* cited by examiner

*Primary Examiner*—Todd E. Manahan
(74) *Attorney, Agent, or Firm*—James D. Christoff

(57) ABSTRACT

An orthodontic bracket has tiewings with cavities for receiving an attachment, such as a hook or a ligating latch. Optionally, the bracket is made in two or more sections or bodies that preferably have cross-sectional configurations similar to each other when viewed in directions perpendicular to the archwire slot. When the bodies are assembled to each other, tiewing portions of each section are located adjacent each other to present a single tiewing.

57 Claims, 4 Drawing Sheets

ORTHODONTIC BRACKET WITH RECESSED ATTACHMENT AND METHOD FOR MAKING THE SAME

BACKGROUND OF THE INVENTION

1. Field of the Invention

This invention broadly relates to an appliance that is used in the course of orthodontic treatment. More particularly, the present invention relates to an orthodontic bracket with an attachment such as a latch, hook or other type of component.

2. Description of the Related Art

Orthodontic treatment involves movement of malpositioned teeth to desired locations along the dental arch. Orthodontic treatment can greatly enhance the patient's appearance once the teeth are moved to desired locations in the oral cavity. In addition, orthodontic treatment can improve the patient's occlusion so that the teeth of one jaw function in a satisfactory manner in combination with the teeth of the opposing jaw.

A variety of orthodontic treatments are known in the art. In one type of treatment, a set of tiny slotted appliances known as brackets are fixed to the patient's teeth and an archwire is then placed in the slots of the brackets. Ends of the archwire are often received in a special type of bracket known as a buccal tube that is fixed to the patient's molar teeth. The archwire has an overall "U"-shaped configuration and forms a track to guide movement of the teeth to desired locations along the dental arch.

Orthodontic brackets are widely available in a number of different configurations and constructed of different materials. Many brackets are made of metallic materials such as stainless steel. Stainless steel brackets are relatively inexpensive and yet sufficiently strong to precisely control movement of the teeth to desired locations.

Other types of orthodontic brackets are made of transparent or translucent materials such as plastic or ceramic. These types of brackets are more difficult to see in the oral cavity when worn by the patient and consequently are considered more aesthetic than metal brackets. Examples of aesthetic ceramic and plastic brackets are described in U.S. Pat. Nos. 4,954,080, 5,439,379 and 5,522,725.

A variety of manufacturing methods are known for making orthodontic brackets, and are often selected based in part upon the choice of materials for the bracket. Stainless steel brackets, for example, are often machined using an automated rotary mill. An example of a method for making orthodontic brackets using a ring milling technique is described in U.S. Pat. No. 2,713,720.

Stainless steel brackets can also be manufactured using a casting technique or a metal injection molding technique. In the casting technique, a quantity of metal heated to a melting temperature is directed into a mold cavity and allowed to cool and harden. In a metal injection molding technique, a quantity of metallic powder along with a binder is forced under pressure into a mold cavity, and the mold is heated until such time as the metal particles have sintered together to form a dense, unified body.

Plastic and ceramic brackets may also be made using different techniques. For example, ceramic brackets and brackets made of relatively hard plastic can be machined to a desired configuration. Alternatively, brackets that are made of some plastic or ceramic materials can be made using a dry pressing technique or an injection molding technique.

Typically, orthodontic brackets have an overall size that is relatively small. More specifically, most orthodontic brackets have overall dimensions that are less than 0.25 inch (6 mm) on each side. As a consequence, it has often been attempted to make orthodontic brackets in one piece as a single, unitary component or at most in two initially separate pieces in order to avoid the necessity of making and assembling several small, separate components.

However, some brackets are provided with attachments that serve particular functions. For example, certain brackets are provided with outwardly extending elongated attachments known as hooks. Hooks are sometimes used by orthodontists during the course of treatment to receive one end of an elastic member, the other end of which is connected to a hook that is attached to another bracket in the oral cavity. The elastic member exerts a force in tension that tends to urge the inter-connected brackets and consequently the associated teeth toward each other.

In the past, other brackets with hooks have been made as an initial single component, by milling or by molding the hook directly to another portion of the bracket. An example of a bracket with an integral hook is described in U.S. Pat. No. 5,395,237. As an alternative, other metal brackets with hooks have been made by brazing or welding a hook to a portion of the bracket. In either instance, it is important to ensure that the resulting connection between the hook and the bracket is secure so that the hook does not detach from remaining portions of the bracket during the course of treatment.

Other types of bracket attachments are also known. For example, some brackets include a movable clip for holding an archwire in the archwire slot of the bracket. Examples of such brackets are described in U.S. Pat. Nos. 4,197,642, 4,698,016, 5,322,435 and 6,168,428 and are often called "self-ligating" brackets.

While the brackets described above have been generally satisfactory, there is a continuing interest in the art to improve manufacturing methods for orthodontic brackets, especially orthodontic brackets with attachments. Preferably, any improved manufacturing methods and the resulting brackets would not unduly increase the overall size of the bracket so that the likelihood of patient discomfort need not be increased.

SUMMARY OF THE INVENTION

The present invention is directed toward an orthodontic bracket having one or more cavities for receiving an attachment. The cavities are located in tiewings of the bracket and consequently occupy a region of the bracket that might otherwise be unused. The cavities provide a convenient mounting location for supporting the attachments in a prominent location, such as in an area near the front of the bracket where the attachment may be best utilized.

Advantageously, the cavities provide a useful and inexpensive means for connecting the attachment to remaining portions of the bracket without necessarily increasing the overall size of the bracket. As such, there is less likelihood that the bracket will protrude into adjacent soft tissue in the oral cavity and cause discomfort to the patient. In addition, by avoiding an increase in the overall size of the bracket, the visibility of the bracket when worn by the patient is not increased and the aesthetic appearance of the bracket in the oral cavity need not be adversely affected.

In more detail, the present invention in one aspect concerns an orthodontic bracket that comprises a first body having a trunk portion, an occlusal tiewing portion, a gingival tiewing portion and an archwire slot portion extending between the occlusal tiewing portion and the gingival tiewing portion. The orthodontic bracket also includes a second body having a trunk portion, an occlusal tiewing portion, a gingival tiewing portion and an archwire slot portion extending between the occlusal tiewing portion and the gingival portion. The first body and the second body are located adjacent each other such that the occlusal tiewing portion of the first body and the occlusal tiewing portion of the second body present a single occlusal tiewing, and the gingival tiewing portion of the first body and the gingival tiewing portion of the second body present a single gingival tiewing.

Another aspect of the present invention is also directed toward an orthodontic bracket. In this aspect, the bracket comprises a first body having a trunk portion, an occlusal tiewing portion, a gingival tiewing portion and an archwire slot portion extending between the occlusal tiewing portion and the gingival tiewing portion. The bracket also includes a second body having a trunk portion, and occlusal tiewing portion, a gingival tiewing portion and an archwire slot portion extending between the occlusal tiewing portion and the gingival tiewing portion. The first body and the second body are located adjacent each other such that the occlusal tiewing portion of the first body and the occlusal tiewing portion of the second body present a single occlusal tiewing, and the gingival tiewing portion of the first body and the gingival tiewing portion of the second body present a single gingival tiewing. The occlusal tiewing portions have outer occlusal tips that engage each other, and the gingival tiewing portions have outer gingival tips that engage each other. A cavity is located between the first body and the second body, and a latch is located at least partially in the cavity for retaining an archwire in the archwire slot.

The present invention is also directed in another aspect to an orthodontic bracket. In this aspect, the bracket includes a base and a body extending outwardly from the base. The body includes an occlusal tiewing, a gingival tiewing, and an archwire slot extending between the occlusal tiewing and the gingival tiewing. The body includes a cavity that extends along occlusal, gingival and lingual sides of the archwire slot. A latch is located at least partially in the cavity for retaining an archwire in the archwire slot.

The present invention is also directed in another aspect to an orthodontic bracket. In this aspect, the bracket includes a first body having a trunk portion, an occlusal tiewing portion and a gingival tiewing portion. The bracket also includes a second body having a trunk portion, an occlusal tiewing portion and a gingival tiewing portion. The first body and the second body are located adjacent each other such that the occlusal tiewing portion of the first body and the occlusal tiewing portion of the second body present a single occlusal tiewing, and the gingival tiewing portion of the first body and the gingival tiewing portion of the second body present a single gingival tiewing. A cavity is located between the first body and the second body. A latch is located at least partially in the cavity for retaining an archwire in the archwire slot.

The present invention is also directed in another aspect to a method of making an orthodontic bracket. In this aspect, the method includes the act of providing a first body having a mesial side and the act of providing a second body having a distal side. The first body is connected to the second body such that the distal side of the second body contacts the mesial side of the first body. A cavity is established between the mesial side of the first body and the distal side of the second body. An attachment is placed in a position at least partially in the cavity.

Another aspect of the invention is directed toward a method of making an orthodontic bracket. The method includes the act of providing a first body having a trunk portion, an occlusal tiewing portion, a gingival tiewing portion and an archwire slot portion extending between the occlusal tiewing portion and the gingival tiewing portion. The method also includes the act of providing a second body having a trunk portion, an occlusal tiewing portion, a gingival tiewing portion and an archwire slot portion extending between the occlusal tiewing portion and the gingival tiewing portion. The method further includes the act of assembling the first body to the second body such that the occlusal tiewing portion of the first body contacts the occlusal tiewing portion of the second body and the gingival tiewing portion of the first body contacts the gingival tiewing portion of the second body.

An additional aspect of the present invention is also directed toward a method of making an orthodontic bracket. This method includes the act of providing a first body having a trunk portion, an occlusal tiewing portion, a gingival tiewing portion and an archwire slot portion extending between the occlusal tiewing portion and the gingival tiewing portion. The method also includes the act of providing a second body having a trunk portion, and occlusal tiewing portion, a gingival tiewing portion and an archwire slot portion extending between the occlusal tiewing portion and the gingival tiewing portion. The method further includes the act of assembling the first body to the second body such that the occlusal tiewing portion of the first body is adjacent the occlusal tiewing portion of the second body and together present a single occlusal tiewing and a gingival tiewing portion of the first body is adjacent a gingival tiewing portion of the second body and together present a single gingival tiewing.

Other aspects of the invention are described in the detailed description set out below and are illustrated in the accompanying drawings.

DETAILED DESCRIPTION OF THE PREFERRED EMBODIMENTS

Figure 1:
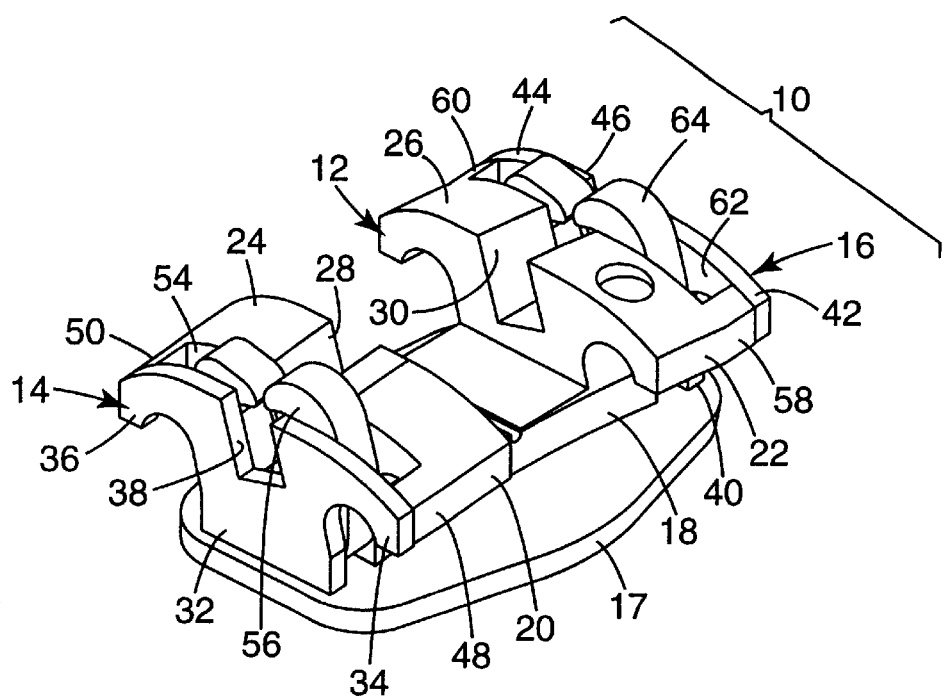
FIG. 1 is a perspective view of an orthodontic bracket according to one embodiment of the present invention.
Figure 2:
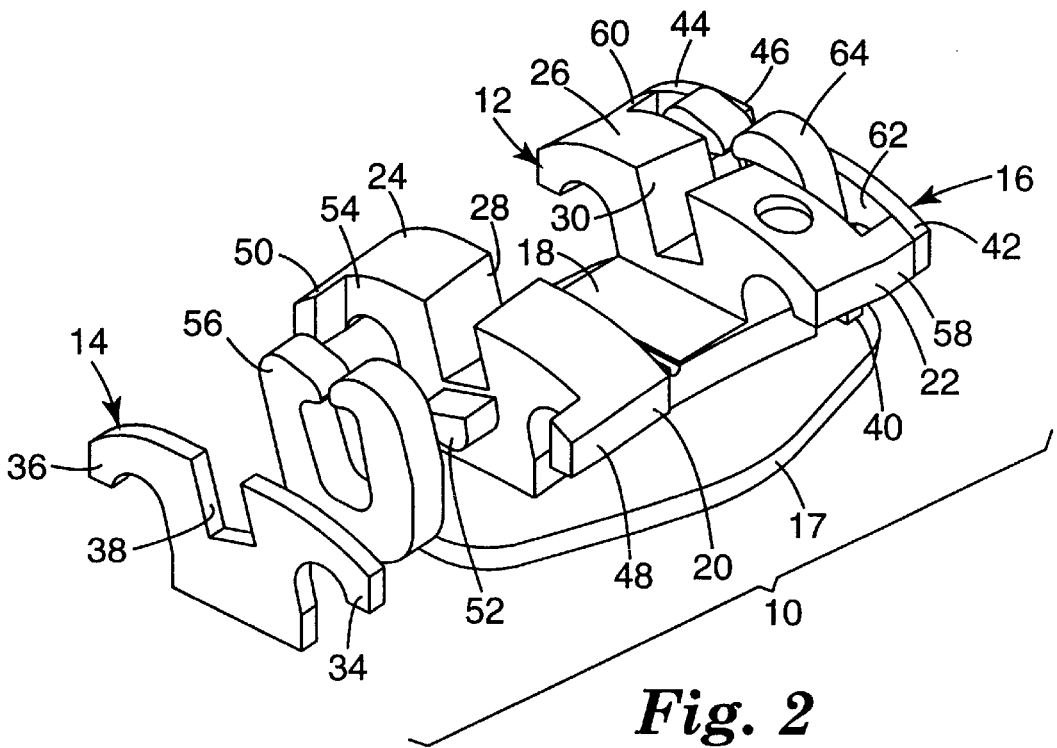
FIG. 2 is a view of the bracket illustrated in FIG. 1, except that the bracket is shown in exploded format as it might appear before assembly.

An orthodontic bracket according to one embodiment of the invention is illustrated in FIGS. 1 and 2 and is broadly designated by the numeral 10. The bracket 10 includes a first body 12, a second body 14 and a third body 16. Each of the bodies 12, 14, 16 is fixed to a bracket base 17.

The first body 12 includes a trunk portion 18 that is located directly adjacent the base 17. The first body 12 also includes first and second occlusal tiewing portions 20, 22 that are spaced apart from each other, and first and second gingival tiewing portions 24, 26 that are spaced apart from each other. An elongated archwire slot portion 28 extends between the first occlusal tiewing portion 20 and the first gingival tiewing portion 24, and an archwire slot portion 30 extends between the second occlusal tiewing portion 22 and the second gingival tiewing portion 26.

The second body 14 also includes a trunk portion 32 that is located adjacent the base 17. The trunk portion 32 is connected to an occlusal tiewing portion 34 as well as a gingival tiewing portion 36 that is spaced from the occlusal tiewing portion 34. An archwire slot portion 38 extends between the tiewing portions 34, 36.

Similarly, the third body 16 of the bracket 10 includes a trunk portion 40 that is adjacent the bracket base 17. The third body 16 includes an occlusal tiewing portion 42 and a gingival tiewing portion 44, both of which are connected to the trunk portion 40. An archwire slot portion 46 extends in the space between the occlusal tiewing portion 42 and the gingival tiewing portion 44.

The first occlusal tiewing portion 20 includes an occlusal tip protrusion 48 that extends outwardly in a mesial direction (i.e., in a direction toward the middle of the patient's dental arch). The first gingival tiewing portion 24 includes a gingival tip protrusion 50 that extends outwardly in a mesial direction. A lingual protrusion 52 (FIG. 2) extends in a mesial direction away from the first body 12 adjacent a lingual side of the archwire slot portion 28.

When the bracket 10 is assembled as shown in FIG. 1, a first cavity 54 is presented between the mesial side of the first body 12 and the distal side (i.e., the side facing away from the middle of the patient's dental arch) of the second body 14. A latch 56 having an overall, generally "C"-shaped configuration is received in the first cavity 54 and is located between the occlusal tip protrusion 48 and the gingival tip protrusion 50. The latch 56 also extends in the space between the lingual protrusion 52 and the base of the bracket 10.

The latch 56 is preferably made from a flat annealed superelastic material having a pickled surface. Preferably, the superelastic material is nitinol having a nickel content of 55.97% by weight and an $A_f$ of 10°±5° C. The nitinol is cold worked to 37.5% and has a thickness in the range of about 0.012 in (0.3 mm) to about 0.016 in (0.4 mm). The latch 56 is first cut in a rough cutting EDM process, and then cut along its edges for an additional one or more times using an EDM process in order to smooth the edges. As another option, the latch 56 is cut from a section of tubing that is made from a shape memory alloy. Suitable shape memory alloys include alloys of nitinol and beta-titanium. The tubing is cut with a slot to form the opposed arm portions that are shown in FIGS. 1 and 2.

The second occlusal tiewing portion 22 includes an occlusal tip protrusion 58 that extends outwardly in a distal direction. The second gingival tiewing portion 26 includes a gingival tip protrusion 60 that extends in a distal direction from the gingival tip of the second gingival tiewing portion 26. The first body 12 also includes a second lingual protrusion that is not shown in the drawings, but is similar to the lingual protrusion 52 and extends in a distal direction away from the first body 12 along the lingual side of the archwire slot portion 30.

A second cavity 62 is presented between the distal side of the first body 12 and the mesial side of the third body 16. A second latch 64 is received in the second cavity 62 and optionally is similar or identical to the latch 56.

When the bracket 10 is assembled as shown in FIG. 1, the third body 16 is connected to the first body 12 by means of the protrusions 48, 50. Optionally, the protrusions 48, 50 may be welded or brazed to the second body 14 in instances where the first body 12 and the second body 14 are made of a metallic material such as Series 304 stainless steel. The lingual protrusion 52 is received between a lingual or tooth-facing section of the latch 56 and a buccolabial side of an archwire slot (described below) and functions to retain the latch 56 in the first cavity 54. Preferably, but not necessarily, the lingual protrusion 52 is welded or brazed to the second body 14.

Similarly, the protrusions 58, 60 function to secure the third body 16 to the first body 12. The lingual protrusion (not shown) adjacent the second cavity 62 functions to hold the second latch 64 in place, but need not be welded or brazed to the third body 16. Preferably, all three of the bodies 12, 14, 16 are also secured to the base 17 of the bracket 10 by a welding (such as laser welding), brazing or other process.

As depicted in FIG. 1, the first occlusal tiewing portion 20 of the first body 12 and the occlusal tiewing portion 34 of the second body 14 together present a single occlusal tiewing on the mesial side of the bracket 10. Similarly, the first gingival tiewing portion 24 of the first body 12 and the gingival tiewing portion 36 of the second body 14 together present a single gingival tiewing on the mesial side of the bracket 10. The occlusal tiewing portions 22, 42 present a single occlusal tiewing on the distal side of the bracket 10, and the gingival tiewing portions 26, 44 present a single gingival tiewing on the distal side of the bracket 10.

The archwire slot portions 28, 30, 38 and 46 present a single elongated archwire slot. Optionally, and as shown in the drawings, the bodies 12, 14, 16 have identical configurations when viewed in reference planes perpendicular to the longitudinal axis of the archwire slot. As a result, the overall appearance of the bracket 10 when assembled is similar (in this embodiment) to a "twin" tiewing bracket having a mesial pair of tiewings and a distal pair of tiewings.

Preferably, the latches 56, 64 are sufficiently flexible to enable the orthodontist to insert an archwire in the archwire slot by pressing the archwire against the latches 56, 64 in locations over the space between the opposed labial or front arm portions of the latches 56, 64. As the archwire is urged against the arm portions, the sides of the latches 56, 64 deflect outwardly away from each other to enable the archwire to be pushed into the center of the latches 56, 64. Once the archwire is located in the archwire slot, the sides of the latches 56, 64 self-deflect and spring back toward each other to their normal, closed orientation as shown in FIGS. 1 and 2 in order to retain the archwire in the archwire slot.

Preferably, the sides of the latches 56, 64 deflect outwardly to enable the latches 56, 64 to assume a slot-open orientation and release the archwire from the archwire slot whenever the force exerted by the archwire on the bracket 10 exceeds a certain minimum value. The minimum value is sufficiently high to prevent the archwire from unintentionally releasing from the archwire slot during the normal course of orthodontic treatment. As such, the archwire can exert forces on the bracket 10 sufficient to carry out the intended treatment program and move the associated tooth as desired. Preferably, the latches 56, 64 release the archwire from the archwire slot in a direction perpendicular and away from the lingual side of the archwire slot whenever the archwire exerts a force in the same direction on the bracket 10 that is in the range of about 0.2 lb (0.1 kg) to about 11 lbs (5 kg), more preferably in the range of about 0.4 lb (0.2 kg) to about 5.5 lbs (2.5 kg), and most preferably in the range of about 0.4 lb (0.2 kg) to about 2.7 lbs (1.25 kg).

To determine the force to release the archwire from the latches 56, 64, an elongated section of archwire is selected having an area in longitudinally transverse section that is complemental to (i.e., substantially fills) the cross-sectional area of the archwire slot. Next, a sling is constructed and is connected to the archwire section in two spaced apart locations that are closely adjacent but not in contact with the mesial and distal sides of the bracket 10. Optionally, the sling is welded or brazed to the archwire section. Next, the sling is pulled away from the bracket 10 while the bracket 10 is held in a stationary position, taking care to ensure that the longitudinal axis of the archwire section does not tip relative to the longitudinal axis of the archwire slot. The force to release the archwire from the latches 56, 64 is determined by use of an Instron testing apparatus connected to the sling, using a crosshead speed of 0.5 in/min (1.3 cm/min.).

Preferably, the minimum value for self-release (i.e., self-opening) of the latches 56, 64 is together substantially less than the force required in the same direction to debond the bracket 10 from the associated tooth. The minimum value for self-release of the latches 56, 64 is preferably less than about one-half of the force required in the same direction to debond the bracket 10 from the associated tooth. For example, if the expected bond strength of the adhesive bond between the bracket 10 and the associated tooth is 16 lbs (7.3 kg) in a buccolabial direction, the latches 56, 64 are constructed to self-release the archwire whenever the archwire exerts a force in the same buccolabial direction on the bracket 10 that is somewhat greater than about 8 lbs (3.6 kg).

The self-releasing latches 56, 64 are a benefit to the practitioner, in that the likelihood of spontaneous debonding of the bracket 10 is substantially reduced. For example, if the practitioner attempts to place a relatively large archwire in the archwire slot and the latches 56, 64 open and self-release the archwire as soon as the practitioner releases the archwire, the practitioner can then use an archwire with less stiffness in its place. As another example, if the archwire is initially held in the archwire slot by the latches 56, 64 and the archwire subsequently exerts a larger force on the bracket 10 (as may occur, for example, when the archwire encounters a hard object such as when the patient is chewing relatively hard food), the latches 56, 64 will deflect to their slot-open orientations to release the archwire so that the bracket 10 does not debond from the tooth. Treatment can then be resumed by merely replacing the archwire in the archwire slot without the need to rebond the base 17 of the bracket 10 to the associated tooth.

Other details and features of the latches 56, 64 are set out in applicant's co-pending U.S. patent application entitled "ORTHODONTIC APPLIANCE WITH SELF-RELEASING LATCH", U.S. Ser. No. 09/848,030, which is expressly incorporated by reference herein.

The base 17 could be constructed in a manner similar to the base of other brackets known in the art. For example, the base 17 could be comprised of a mesh screen with a foil backing that is connected to the bodies 12, 14, 16. Preferably, the base 17 has a concave compound contour that matches the convex compound contour of the patient's tooth surface. Optionally, the base 17 may be provided with grooves, particles, recesses, undercuts, a chemical bond enhancement material or any other material or structure or any combination of the foregoing that facilitates bonding of the bracket 10 directly to the patient's tooth enamel.

Other options for the bracket 10 are also possible. For example, the protrusions 48, 50, 52 could be initially made as part of the second body 14 instead of the first body 12, and during subsequent assembly the protrusions 48, 50 are secured to the first body 12. In addition, the cavities 54, 62 could have shapes other than that shown in the drawings. Moreover, the width of the tiewing portions 20, 22, 24, 26 may be reduced in a mesial-distal direction, so that they are approximately the same width as the mesial-distal width of the tiewing portions 34, 36, 42, 44. Also, the latches 56, 64 may also be varied from the construction illustrated. Other examples of suitable constructions are described in the aforementioned pending U.S. patent application, Ser. No. 09/848,030.

Figure 3:
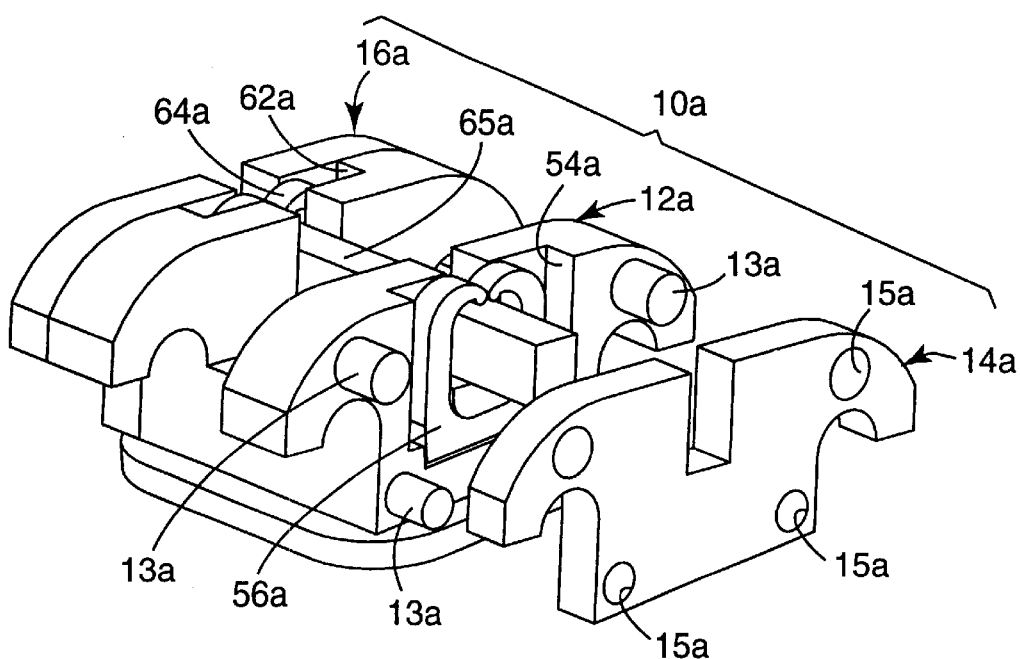
FIG. 3 is a perspective view of an orthodontic bracket according to another embodiment of the invention.

An orthodontic bracket 10a according to another embodiment of the invention is illustrated in FIG. 3 and is shown in exploded format before assembly has been completed. Except for the differences set out below, the bracket 10a is essentially the same as the bracket 10 described above. As such, a description of the common features and aspects need not be repeated.

The bracket 10a includes a first body 12a, a second body 14a and a third body 16a. A first cavity 54a and a second cavity 62a are formed in the first body 12a. A first latch 56a is received in the first cavity 54a, and a second latch 64a is received in the second cavity 62a. In FIG. 3, an archwire 65a is depicted as it might appear when received in an archwire slot of the bracket 10a.

The first body 12a includes four mesial protrusions 13a (only three are shown) that extend in a mesial direction parallel to the longitudinal axis of an archwire slot of the bracket 10a. Each of the protrusions 13a has an overall cylindrical configuration, although other shapes are also possible. Each of the protrusions 13a is received in a corresponding, mating cylindrical hole 15a that is formed in the second body 14a.

Although not shown in FIG. 3, the distal side of the first body 12a also has four protrusions that extend in a distal direction and are somewhat similar to the protrusions 13a. Each of the distally-extending protrusions is received in mating holes formed in the third body 16a.

The second body 14a and the third body 16a may be fixed to the first body 12a by any suitable means. For example, once the protrusions 13a are fully received in the holes 15a, a welding or brazing process may be used to secure the bodies 12a, 14a together. Optionally, an interference fit relationship between the protrusions 13a and the holes 15a may be provided. Additionally, the number of protrusions (such as protrusions 13a) is not critical and may be a number less than or greater than set out above.

Figure 4:
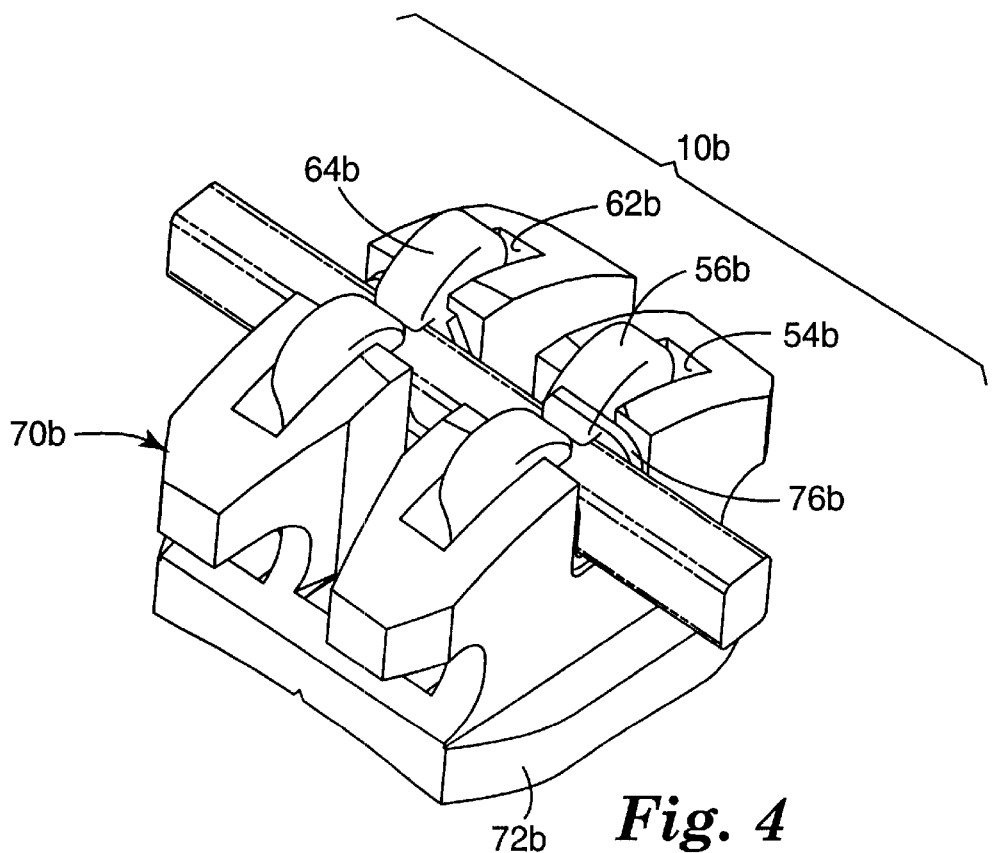
FIG. 4 is a perspective view of an orthodontic bracket that is constructed in accordance with yet another embodiment of the invention.
Figure 5:
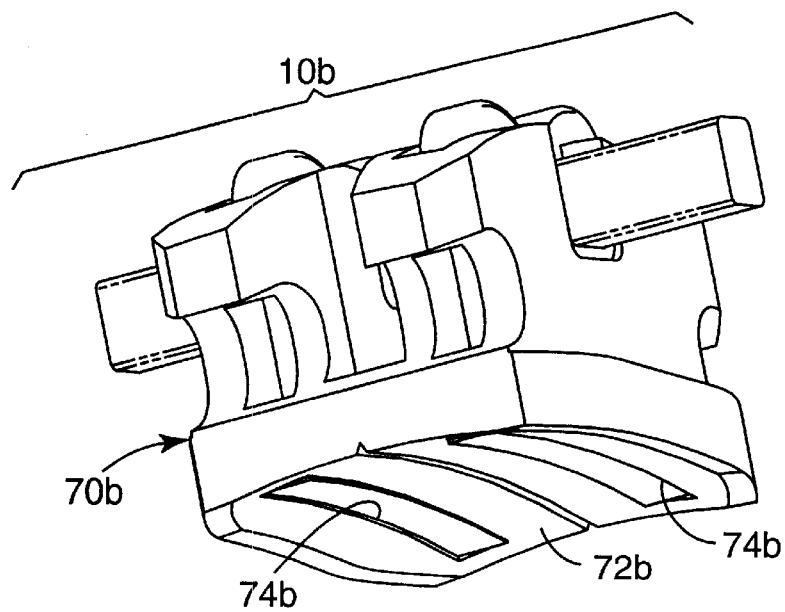
FIG. 5 is a perspective view the orthodontic bracket illustrated in FIG. 4, except that the illustration in FIG. 5 shows the bracket from a different direction.

An orthodontic bracket 10b according to another embodiment of the invention is illustrated in FIGS. 4 and 5. In this embodiment, the bracket 10b is comprised of a single body 70b having an integrally connected base portion 72b. The body 70b has a first cavity 54b that receives a first latch 56b and a second cavity 62b that receives a second latch 64b.

The latches 56b, 64b are inserted into the body 70b through two slots 74b in the base portion 72b. The slots 74b are depicted in FIG. 5. The slots 74b are connected to the cavities 54b, 62b and allow the latches 56b, 64b to be placed within the body 70b and around the archwire slot. Once the latches 56b, 64b are in place, the slots 74b are preferably closed as shown in FIG. 5. For example, the slots 74b may be filled by use of a photocurable orthodontic adhesive such as Transbond brand adhesive from 3M Unitek Corporation. As another option, the slots 74b may be filled with a section of ceramic or other material that is secured in place by an adhesive.

Although not shown in the drawings, one or more metallic pins are optionally placed in the bracket body 70b when the body 70b is made of a ceramic or other relatively brittle material. The pins extend in a mesial-distal direction. The pins are located between the lingual side of the archwire slot and the lingual leg of the latches 56b, 64b (each of which has a configuration similar to the latch 56a illustrated in FIG. 3). The pins retain the latches 56b, 64b in the cavities 54b, 62b respectively. The pins are sufficiently flexible to enable the bracket 10b to be debonded from the associated tooth by squeezing mesial and distal sides of the bracket 10b together and help to ensure that fragments of the bracket 10b are not separated during debonding.

Optionally, the bracket 10b is made of a light-transmitting ceramic material such as translucent polycrystalline alumina. Preferably, the ceramic material exhibits translucency characteristics similar to the ceramic material described in applicant's U.S. Pat. No. 4,954,080, which is incorporated by reference herein. Preferably, the bracket 10b can be debonded from the tooth in the manner set out in U.S. Pat. No. 5,439,379, which is also incorporated by reference herein.

Optionally, the orthodontic bracket 10b has an archwire slot liner 76b. The archwire slot liner 76b extends between mesial and distal sections of the bracket 10b and is preferably made of a metallic material. Other aspects of the archwire slot liner 76b and method of connecting the archwire slot liner 76b to the body 70b are described in U.S. Pat. Nos. 5,358,402 and 5,380,196, which are also incorporated by reference herein.

Figure 6:
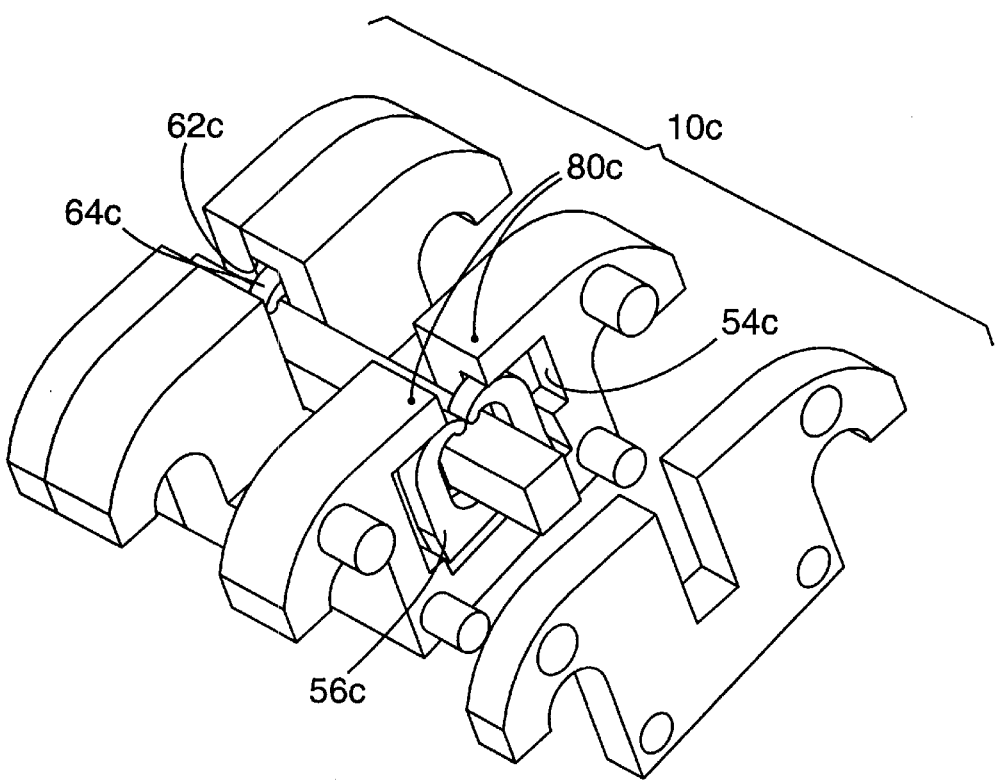
FIG. 6 is a perspective, exploded view of an orthodontic bracket that is constructed in accordance with still another embodiment of the invention.

An orthodontic bracket 10c according to another embodiment of the invention is shown in FIG. 6. Except as described below, the orthodontic bracket 10c is essentially the same as the orthodontic bracket 10a that is illustrated in FIG. 3. A base of the bracket 10c is not shown.

The bracket 10c includes a first cavity 54c that receives a first latch 56c. As shown, the front or buccolabial side of the latch 54c is submerged within the bracket 10c and as such does not protrude outwardly from a front face of the associated tiewing. A pair of flanges 80c extends over the cavity 54c in order to help retain the latch 56c in the cavity 54c.

The bracket 10c includes a second latch 64c that is received in a second cavity 62c. The submerged latches 56c, 64c are a benefit in that the overall dimension of the bracket in a labial-lingual direction is not extended by the presence of the latches 56c, 64c.

Figure 7:
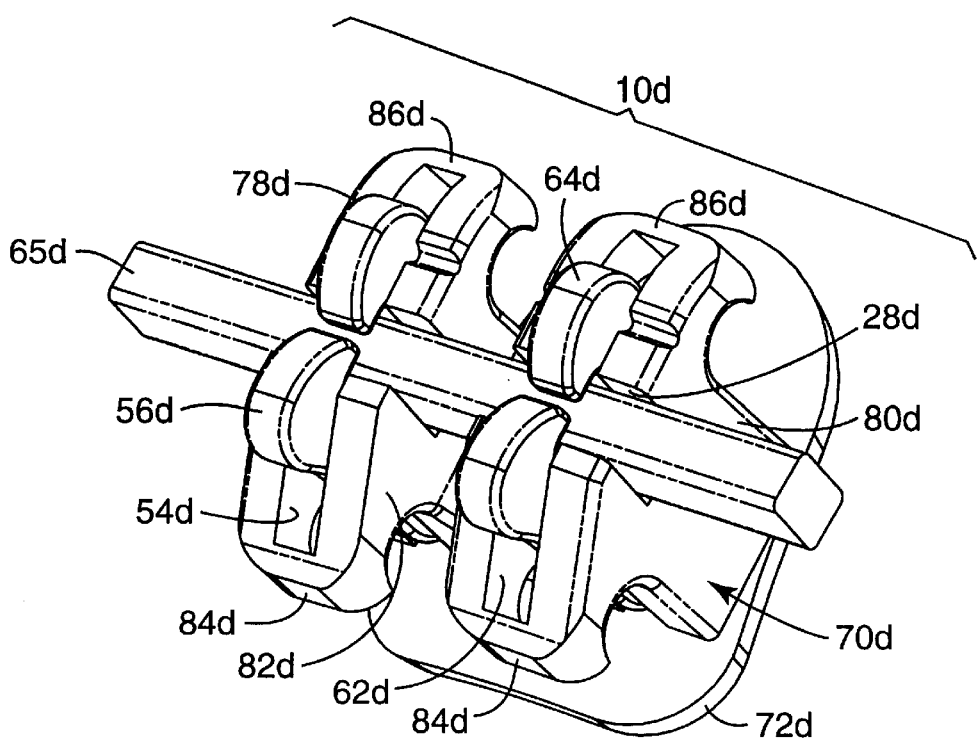
FIG. 7 is a perspective view of an orthodontic bracket that is constructed according to a further embodiment of the invention.
Figure 8:
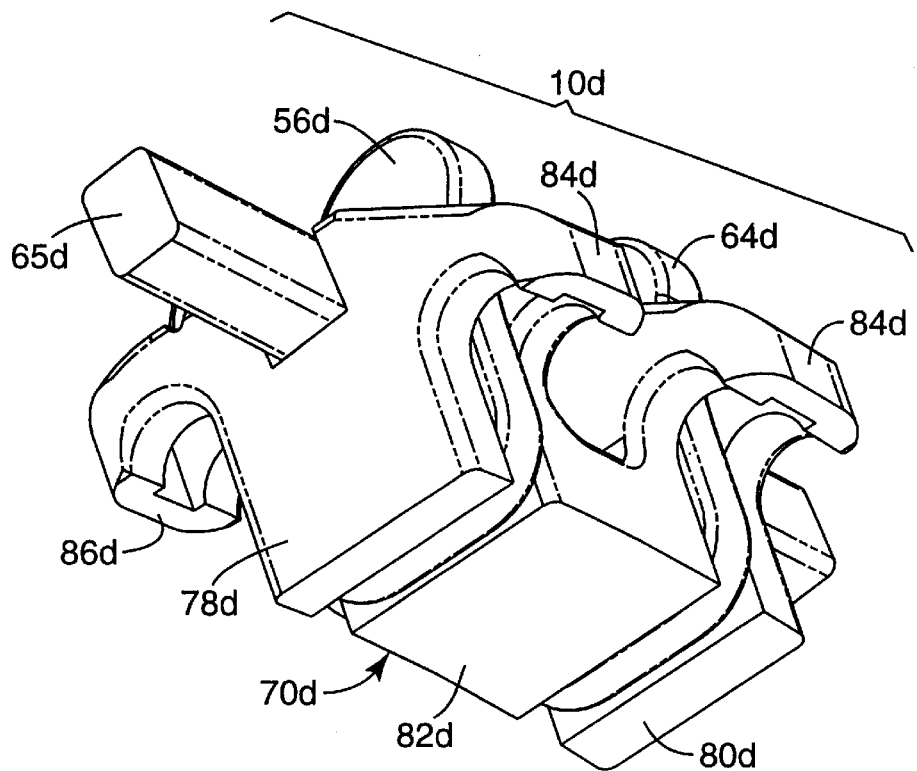
FIG. 8 is a perspective view of the orthodontic bracket shown in FIG. 7, except that the illustration in FIG. 8 shows the bracket from a different direction and does not show a base of the bracket.

An orthodontic bracket 10d according to another embodiment of the invention is illustrated in FIGS. 7 and 8 along with a section of an archwire 65d. The orthodontic bracket 10d is similar to the bracket 10b except for the differences set out below.

The bracket 10d is comprised of a body 70d and a base 72d that is secured to the body 70d. The base 72d is omitted in FIG. 8 for purposes of illustration. The body 70d has a first cavity 54d that receives a first latch 56d and a second cavity 62d that receives a second latch 64d.

The body 70d includes a mesial body portion 78d, a distal body portion 80d and a central body portion 82d that lies between the mesial and distal body portions 78d, 80d. The central body portion 82d is connected to the mesial and distal body portions 78d, 80d by outer occlusal tips 84d of the occlusal tiewings and by outer gingival tips 86d of the gingival tiewings. In addition, the central body portion 82d is connected to the mesial and distal body portions 78d, 80d by internal sections that extend in generally mesial and distal directions away from the central body portion 82d. The internal sections are located on a lingual side of an archwire slot 28d. The internal sections are not shown in the drawings, but are preferably similar in shape and location to the protrusion 52 that is shown in FIG. 2.

During assembly of the bracket 10d, the latches 56d, 64d are placed in the cavities 54d, 62d respectively by moving each latch 56d, 64d in a buccolabial direction until each is located in a position surrounding the archwire slot 28d and the respective internal section mentioned above. Subsequently, the base 72d is fixed to the body 70d. Preferably, the base 72d is directly connected to the bottom of each of the portions 78d, 80d, 82d in order to provide additional strength and stability to the resulting bracket 10d. If the base 72d and the body 70d are made of metallic materials, a welding or brazing process may be used to connect the base 72d to the body 70d.

The brackets 10–10d may be made by any one of a number of manufacturing methods, including milling and injection molding techniques. Optionally, the brackets 10–10d are made by a metal injection molding technique. The brackets 10–10d may also be made of plastic materials in addition to the metal and ceramic materials mentioned above.

The brackets 10–10d are an advantage in that the tips of the tiewings are generally solid and generally lack recesses that might otherwise retain food or other debris. Preferably, the tips of the tiewings are closed on three sides, including the labial side, the lingual side and the outer side (i.e., the occlusal side in instances where the tiewing is an occlusal tiewing, and the gingival side in instances where the tiewing is a gingival tiewing). The closed, smooth appearance also helps to avoid snagging a separate wire or elastomeric ligature in treatment techniques where a ligature is used.

Additionally, the cavities 54–54d, 62–62d are an advantage because they provide a convenient space for receiving a latch such as latches 56–56d, 64–64d. As a result, the latches need not be located along mesial and distal sides of the brackets and do not necessarily increase the overall mesial-distal width of the bracket. The brackets can therefore be made, if desired, in a relatively compact size in order to decrease their visibility in the oral cavity and also reduce the likelihood that the bracket will impinge against the soft tissue of the patient in an irritating manner.

Furthermore, the cavities may be advantageously used to receive other attachments as well. For example, the cavities may be used to receive a hook that extends outwardly from the associated tiewing. In that instance, the cavity and the portion of the hook that is received in the cavity may be made with mating configurations that are optionally mechanically interlocked with each other in order to retain the hook in place.

A number of other variations are also possible. For example, the brackets may have only a single occlusal and gingival tiewing. As another option, the brackets may be adapted for use on the lingual surfaces of the patient's teeth, or may be adapted to serve as buccal tube brackets. Accordingly, the invention should not be deemed limited to the specific embodiments that are described in detail above, but instead only by a fair scope of the claims that follow along with their equivalents.

What is claimed is:

1. An orthodontic bracket comprising:
   a first body having a trunk portion, an occlusal tiewing portion, a gingival tiewing portion and an archwire slot portion extending between the occlusal tiewing portion and the gingival tiewing portion; and
   a second body having a trunk portion, an occlusal tiewing portion, a gingival tiewing portion and an archwire slot portion extending between the occlusal tiewing portion and the gingival tiewing portion,
   wherein the first body and the second body are located adjacent each other such that the occlusal tiewing portion of the first body and the occlusal tiewing portion of the second body present a single occlusal tiewing, and the gingival tiewing portion of the first body and the gingival tiewing portion of the second body present a single gingival tiewing.

2. An orthodontic bracket according to claim 1 wherein the occlusal tiewing portions have outer occlusal tips that engage each other, and wherein the gingival tiewing portions have outer gingival tips that engage each other.

3. An orthodontic bracket according to claim 1 wherein the archwire slot portion of the first body and the archwire slot portion of the second body present a single archwire slot having a longitudinal axis, and wherein the first body and the second body have cross-sectional configurations that are substantially the same when viewed in reference planes substantially perpendicular to the longitudinal axis of the archwire slot.

4. An orthodontic bracket according to claim 1 wherein the first body also includes a second occlusal tiewing portion, a second gingival tiewing portion and a second archwire slot portion extending between the second occlusal tiewing portion and the second gingival tiewing portion, and wherein the bracket also includes a third body having a trunk portion, an occlusal tiewing portion, a gingival tiewing portion and an archwire slot portion extending between the occlusal tiewing portion and the gingival tiewing portion, and wherein the first body and the third body are located adjacent each other such that the second occlusal tiewing portion of the first body and the occlusal tiewing portion of the third body present a second single occlusal tiewing, and the second gingival tiewing portion of the first body and the gingival tiewing portion of the third body present a second single gingival tiewing.

5. An orthodontic bracket according to claim 4 wherein the archwire slot portions of the first body, the second body and the third body combine to present an archwire slot having a longitudinal axis, and wherein the first body, the second body and the third body have cross-sectional configurations that are substantially the same when viewed in reference planes substantially perpendicular to the longitudinal axis of the archwire slot.

6. An orthodontic bracket according to claim 1 wherein the archwire slot portions of the first body and the second body together present an archwire slot having a longitudinal axis, and wherein at least one of the first body and the second body includes one or more protrusions that extend in a direction generally parallel to the longitudinal axis of the archwire slot and engage the other of the first body and the second body.

7. An orthodontic bracket according to claim 6 wherein at least one protrusion of one of the bodies is received in a hole of the other body.

8. An orthodontic bracket according to claim 6 wherein at least one protrusion has an overall cylindrical configuration.

9. An orthodontic bracket according to claim 1 and including a base, wherein the base is directly secured to both the first body and the second body.

10. An orthodontic bracket according to claim 1 and including a cavity located between the first body and the second body.

11. An orthodontic bracket comprising:
    a first body having a trunk portion, an occlusal tiewing portion, a gingival tiewing portion and an archwire slot portion extending between the occlusal tiewing portion and the gingival tiewing portion;
    a second body having a trunk portion, an occlusal tiewing portion, a gingival tiewing portion and an archwire slot portion extending between the occlusal tiewing portion and the gingival tiewing portion,
    wherein the first body and the second body are located adjacent each other such that the occlusal tiewing portion of the first body and the occlusal tiewing portion of the second body present a single occlusal tiewing, and the gingival tiewing portion of the first body and the gingival tiewing portion of the second body present a single gingival tiewing, wherein the occlusal tiewing portions have outer occlusal tips that engage each other, and wherein the gingival tiewing portions have outer gingival tips that engage each other;
    a cavity located between the first body and the second body; and
    a latch located at least partially in the cavity for retaining an archwire in the archwire slot.

12. An orthodontic bracket according to claim 11 wherein the occlusal tiewing portions have outer occlusal tips that engage each other, and wherein the gingival tiewing portions have outer gingival tips that engage each other.

13. An orthodontic bracket according to claim 11 wherein the archwire slot portion of the first body and the archwire slot portion of the second body present a single archwire slot having a longitudinal axis, and wherein the first body and the second body have cross-sectional configurations that are substantially the same when viewed in reference planes substantially perpendicular to the longitudinal axis of the archwire slot.

14. An orthodontic bracket according to claim 11 wherein the first body also includes a second occlusal tiewing portion, a second gingival tiewing portion and a second archwire slot portion extending between the second occlusal tiewing portion and the second gingival tiewing portion, and wherein the bracket also includes a third body having a trunk portion, an occlusal tiewing portion, a gingival tiewing portion and an archwire slot portion extending between the occlusal tiewing portion and the gingival tiewing portion, and wherein the first body and the third body are located adjacent each other such that the second occlusal tiewing portion of the first body and the occlusal tiewing portion of the third body present a second single occlusal tiewing, and the second gingival tiewing portion of the first body and the gingival tiewing portion of the third body present a second single gingival tiewing.

15. An orthodontic bracket according to claim 14 wherein the archwire slot portions of the first body, the second body and the third body combine to present an archwire slot having a longitudinal axis, and wherein the first body, the second body and the third body have cross-sectional configurations that are substantially the same when viewed in reference planes substantially perpendicular to the longitudinal axis of the archwire slot.

16. An orthodontic bracket according to claim 11 wherein the archwire slot portions of the first body and the second body together present an archwire slot having a longitudinal axis, and wherein at least one of the first body and the second body includes one or more protrusions that extend in a direction generally parallel to the longitudinal axis of the archwire slot and engage the other of the first body and the second body.

17. An orthodontic bracket according to claim 16 wherein at least one protrusion of one of the bodies is received in a hole of the other body.

18. An orthodontic bracket according to claim 16 wherein at least one protrusion has an overall cylindrical configuration.

19. An orthodontic bracket according to claim 11 and including a base, wherein the base is directly secured to both the first body and the second body.

20. An orthodontic bracket according to claim 11 wherein the latch has an overall generally "C"-shaped configuration.

21. An orthodontic bracket comprising:
a base;
a body extending outwardly from the base, the body including an occlusal tiewing, a gingival tiewing, an archwire slot extending between the occlusal tiewing and the gingival tiewing, and wherein the body includes a cavity that extends along occlusal, gingival and lingual sides of the archwire slot; and
a latch located at least partially in the cavity for retaining an archwire in the archwire slot, wherein the bracket also includes a second occlusal tiewing and a second gingival tiewing, a second cavity and a second latch located at least partially in the second cavity for retaining an archwire in the archwire slot.

22. An orthodontic bracket according to claim 21 wherein the latch has an overall generally "C"-shaped configuration.

23. An orthodontic bracket according to claim 21 wherein the base includes a slot for placing the latch in the cavity.

24. An orthodontic bracket according to claim 23 wherein the slot is closed after the latch is located in the cavity.

25. An orthodontic bracket comprising:
a base;
a body extending outwardly from the base, the body including an occlusal tiewing, a gingival tiewing, an archwire slot extending between the occlusal tiewing and the gingival tiewing, and wherein the body includes a cavity that extends along occlusal, gingival and lingual sides of the archwire slot; and
a latch located at least partially in the cavity for retaining an archwire in the archwire slot, wherein the latch opens to admit an archwire in the archwire slot by pressing the archwire against the latch in a direction toward the base of the bracket.

26. An orthodontic bracket according to claim 25 wherein the latch releases the archwire from the archwire slot in a certain direction whenever the archwire exerts a force on the latch in the same direction that is in the range of about 0.1 kg to about 5 kg.

27. An orthodontic bracket according to claim 25 wherein the occlusal tiewing and the gingival tiewing each include a labial opening that extends into the cavity.

28. An orthodontic bracket according to claim 27 wherein the latch extends through the openings.

29. An orthodontic bracket comprising:
a base;
a body extending outwardly from the base, the body including an occlusal tiewing, a gingival tiewing, an archwire slot extending between the occlusal tiewing and the gingival tiewing, and wherein the body includes a cavity that extends along occlusal, gingival and lingual sides of the archwire slot; and
a latch located at least partially in the cavity for retaining an archwire in the archwire slot, wherein the occlusal tiewing and the gingival tiewing each include a buccolabial side, and wherein the latch is located entirely in a lingual direction relative to the buccolabial side.

30. An orthodontic bracket comprising:
a first body having a trunk portion, an occlusal tiewing portion and a gingival tiewing portion;
a second body having a trunk portion, an occlusal tiewing portion and a gingival tiewing portion, wherein the first body and the second body are located adjacent each other such that the occlusal tiewing portion of the first body and the occlusal tiewing portion of the second body present a single occlusal tiewing, and the gingival tiewing portion of the first body and the gingival tiewing portion of the second body present a single gingival tiewing;
a cavity located between the first body and the second body; and
a latch located at least partially in the cavity for retaining an archwire in the archwire slot.

31. An orthodontic bracket according to claim 30 wherein the occlusal tiewing portions have outer occlusal tips that engage each other, and wherein the gingival tiewing portions have outer gingival tips that engage each other.

32. An orthodontic bracket according to claim 30 wherein the bracket includes an elongated archwire slot, and wherein the first body and the second body have cross-sectional configurations that are substantially the same when viewed in reference planes substantially perpendicular to the longitudinal axis of the archwire slot.

33. An orthodontic bracket according to claim 30 wherein the first body also includes a second occlusal tiewing portion and a second gingival tiewing portion, and wherein the bracket also includes a third body having a trunk portion, an occlusal tiewing portion and a gingival tiewing portion, wherein the first body and the third body are located adjacent each other such that the second occlusal tiewing portion of the first body and the occlusal tiewing portion of the third body present a second single occlusal tiewing, and the second gingival tiewing portion of the first body and the gingival tiewing portion of the third body present a second single gingival tiewing.

34. An orthodontic bracket according to claim 30 wherein the bracket includes an elongated archwire slot, and wherein at least one of the first body and the second body includes one or more protrusions that extend in a direction generally parallel to the longitudinal axis of the archwire slot and engage the other of the first body and the second body.

35. An orthodontic bracket according to claim 34 wherein at least one protrusion of one of the bodies is received in a hole of the other body.

36. An orthodontic bracket according to claim 30 wherein the latch has an overall generally "C"-shaped configuration.

37. A method of making an orthodontic bracket comprising:
providing a first body having a mesial side;
providing a second body having a distal side;
connecting the first body to the second body such that the distal side of the second body contacts the mesial side of the first body;
establishing a cavity located between the mesial side of the first body and the distal side of the second body; and placing an attachment in a position at least partially in the cavity.

38. A method of making an orthodontic bracket according to claim 37 wherein the act of placing an attachment in a position at least partially in the cavity includes the act of placing a latch in a position at least partially in the cavity.

39. A method of making an orthodontic bracket according to claim 38, the act of providing a first body includes the acts of providing an occlusal tiewing portion of the first body and a gingival tiewing portion of the first body, wherein the act of providing a second body includes the acts of providing an occlusal tiewing portion of the second body and a gingival tiewing portion of the second body, and wherein the act of placing a latch in a position at least partially in the cavity includes the act of locating a first section of the latch between the occlusal tiewing portions of the first body and the second body and also includes the act of locating a second section of the latch between the gingival tiewing portions of the first body and the second body.

40. A method of making an orthodontic bracket according to claim 37 and including the act of securing a bracket base directly to the first body and the second body.

41. A method of making an orthodontic bracket according to claim 37 wherein the act of connecting the first body to the second body includes the act of placing a protrusion of one body into a hole of the other body.

42. A method of making an orthodontic bracket comprising:
   providing a first body having a trunk portion, an occlusal tiewing portion, a gingival tiewing portion and an archwire slot portion extending between the occlusal tiewing portion and the gingival tiewing portion;
   providing a second body having a trunk portion, an occlusal tiewing portion, a gingival tiewing portion and an archwire slot portion extending between the occlusal tiewing portion and the gingival tiewing portion; and
   assembling the first body to the second body such that the occlusal tiewing portion of the first body contacts the occlusal tiewing portion of the second body and the gingival tiewing portion of the first body contacts the gingival tiewing portion of the second body.

43. A method of making an orthodontic bracket according to claim 42 wherein the act of assembling the first body to the second body includes the act of establishing a cavity between the first body and the second body.

44. A method of making an orthodontic bracket according to claim 43 and including the act of placing a latch at least partially in the cavity.

45. A method of making an orthodontic bracket according to claim 44 wherein the act of placing the latch at least partially in the cavity includes the act of locating a first section of the latch between the occlusal tiewing portions and a second section of the latch between the gingival tiewing portions.

46. A method of making an orthodontic bracket according to claim 45 wherein the act of assembling the first body to the second body includes the act of forming an archwire slot by combining the archwire slot portion of the first body and the archwire slot portion of the second body, wherein the latch includes a tooth-facing section between the first section and the second section, and wherein the act of placing the latch at least partially in the cavity includes the act of spacing the tooth-facing section from the archwire slot.

47. A method of making an orthodontic bracket according to claim 46 wherein the act of spacing the tooth-facing section from the archwire slot includes the act of providing a protrusion between the tooth-facing section and the archwire slot.

48. A method of making an orthodontic bracket according to claim 42 and including the act of securing a bracket base directly to the trunk portion of the first body and the trunk portion of the second body.

49. A method of making an orthodontic bracket according to claim 42 wherein the act of assembling the first body to the second body includes the act of placing a protrusion of one body into a hole of the other body.

50. A method of making an orthodontic bracket comprising:
   providing a first body having a trunk portion, an occlusal tiewing portion, a gingival tiewing portion and an archwire slot portion extending between the occlusal tiewing portion and the gingival tiewing portion;
   providing a second body having a trunk portion, an occlusal tiewing portion, a gingival tiewing portion and an archwire slot portion extending between the occlusal tiewing portion and the gingival tiewing portion; and
   assembling the first body to the second body such that the occlusal tiewing portion of the first body is adjacent the occlusal tiewing portion of the second body and together present a single occlusal tiewing, and the gingival tiewing portion of the first body is adjacent the gingival tiewing portion of the second body and together present a single gingival tiewing.

51. A method of making an orthodontic bracket according to claim 50 wherein the act of assembling the first body to the second body includes the act of establishing a cavity between the first body and the second body.

52. A method of making an orthodontic bracket according to claim 51 and including the act of placing a latch within the cavity.

53. A method of making an orthodontic bracket according to claim 52 wherein the act of placing the latch within the cavity includes the act of locating a first section of the latch between the occlusal tiewing portions and a second section of the latch between the gingival tiewing portions.

54. A method of making an orthodontic bracket according to claim 53 wherein the act of assembling the first body to the second body includes the act of forming an archwire slot by combining the archwire slot portion of the first body and the archwire slot portion of the second body, wherein the latch includes a tooth-facing section between the first section and the second section, and wherein the act of placing the latch within the cavity includes the act of spacing the tooth-facing section from the archwire slot.

55. A method of making an orthodontic bracket according to claim 54 wherein the act of spacing the tooth-facing section from the archwire slot includes the act of providing a protrusion between the tooth-facing section and the archwire slot.

56. A method of making an orthodontic bracket according to claim 50 and including the act of securing a bracket base directly to the trunk portion of the first body and the trunk portion of the second body.

57. A method of making an orthodontic bracket according to claim 50 wherein the act of assembling the first body to the second body includes the act of placing a protrusion of one body into a hole of the other body.

* * * * *